(12) United States Patent
Yoshino et al.

(10) Patent No.: US 9,113,775 B2
(45) Date of Patent: Aug. 25, 2015

(54) ENDOSCOPE SYSTEM

(71) Applicant: OLYMPUS CORPORATION, Tokyo (JP)

(72) Inventors: Masahiro Yoshino, Sagamihara (JP); Yoshinari Okita, Hachioji (JP); Mitsuhiro Ito, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/161,823

(22) Filed: Jan. 23, 2014

(65) Prior Publication Data

US 2014/0180012 A1  Jun. 26, 2014

Related U.S. Application Data

(63) Continuation of application No. PCT/JP2013/063302, filed on May 13, 2013.

(30) Foreign Application Priority Data

Sep. 13, 2012  (JP) ................................. 2012-201963

(51) Int. Cl.
*A61B 1/06* (2006.01)
*A61B 1/04* (2006.01)
(Continued)

(52) U.S. Cl.
CPC ......... *A61B 1/00172* (2013.01); *A61B 1/00006* (2013.01); *A61B 1/00096* (2013.01);
(Continued)

(58) Field of Classification Search
CPC ........... A61B 1/00163; A61B 1/00172; A61B 1/00165; A61B 1/0167; A61B 1/06; A61B 1/0607; A61B 1/0615; A61B 1/0623; A61B 1/07; A61B 1/0661; A61B 1/0669; A61B 1/00025
USPC ......... 600/101, 108, 109, 117, 160, 178, 179, 600/180, 182
See application file for complete search history.

(56) References Cited

U.S. PATENT DOCUMENTS 6,845,190 B1 * 1/2005 Smithwick et al. ............. 385/25
7,129,472 B1 10/2006 Okawa et al.
(Continued)

FOREIGN PATENT DOCUMENTS

EP    1 142 529 A1   10/2001
JP    2001-174744 A   6/2001
(Continued)

*Primary Examiner* — Anhtuan T Nguyen
*Assistant Examiner* — William Chou
(74) *Attorney, Agent, or Firm* — Scully, Scott, Murphy & Presser, PC

(57) ABSTRACT

An endoscope system includes: a light transmitting section for transmitting illuminating light and emit the light from a light exit surface; a light receiving section for receiving return light of the light emitted from the light exit surface; a light guiding section for allowing the light to be incident on the light receiving section by totally reflecting return light from a subject or the emitted light at least one or more times; a driving section for allowing an end portion having the light exit surface of the light transmitting section to be swung; a light detecting section for detecting the light received through the light guiding section, as a signal; and a control section for, if the pattern of fluctuations in the signal level by the light detected by the light detected section does not correspond to the predetermined pattern of fluctuations, performing control for lowering a quantity of the illuminating light.

8 Claims, 13 Drawing Sheets

(51) Int. Cl.
*A61B 1/00* (2006.01)
*A61B 1/07* (2006.01)
*G02B 23/24* (2006.01)
*G02B 23/26* (2006.01)
*G02B 26/10* (2006.01)

(52) U.S. Cl.
CPC ............... *A61B1/00165* (2013.01); *A61B 1/06* (2013.01); *A61B 1/0661* (2013.01); *A61B 1/07* (2013.01); *G02B 23/2469* (2013.01); *G02B 23/26* (2013.01); *G02B 26/103* (2013.01)

(56) References Cited

U.S. PATENT DOCUMENTS

| | | | |
|---|---|---|---|
| 8,305,432 B2* | 11/2012 | Johnston | 348/65 |
| 2007/0213618 A1* | 9/2007 | Li et al. | 600/476 |
| 2008/0058629 A1* | 3/2008 | Seibel et al. | 600/368 |
| 2008/0249369 A1* | 10/2008 | Seibel et al. | 600/182 |
| 2008/0281159 A1* | 11/2008 | Johnston et al. | 600/160 |
| 2009/0026888 A1 | 1/2009 | Melville | |
| 2009/0135280 A1* | 5/2009 | Johnston et al. | 348/262 |
| 2009/0137893 A1* | 5/2009 | Seibel et al. | 600/407 |
| 2010/0137684 A1 | 6/2010 | Shibasaki et al. | |
| 2011/0015528 A1 | 1/2011 | Kobayashi | |

FOREIGN PATENT DOCUMENTS

| | | |
|---|---|---|
| JP | 2010-131112 A | 6/2010 |
| JP | 2010-534862 A | 11/2010 |
| JP | 2010-268961 A | 12/2010 |
| JP | 2011-019706 A | 2/2011 |
| WO | WO 01/24686 A1 | 4/2001 |
| WO | WO 2009/014525 A1 | 1/2009 |

* cited by examiner

——— FIRST DRIVE SIGNAL (X AXIS DIRECTION)
- - - - - SECOND DRIVE SIGNAL (Y AXIS DIRECTION)

—— FIRST DRIVE SIGNAL (X AXIS DIRECTION)
----- SECOND DRIVE SIGNAL (Y AXIS DIRECTION)

ENDOSCOPE SYSTEM

CROSS REFERENCE TO RELATED APPLICATION

This application is a continuation application of PCT/JP2013/063302 filed on May 13, 2013 and claims benefit of Japanese Application No. 2012-201963 filed in Japan on Sep. 13, 2012, the entire contents of which are incorporated herein by this reference.

BACKGROUND OF THE INVENTION

1. Field of the Invention

The present invention relates to an endoscope system, and more particularly, to an endoscope system that scans an object to acquire an image thereof.

2. Description of the Related Art

In an endoscope used in a medical field, in order to reduce a burden on subjects, various techniques have been proposed for achieving a reduction in diameter of an endoscope insertion portion to be inserted into a body cavity of a subject. Known examples of such techniques are an optical scanning endoscope having no solid image pickup device in its section corresponding to the insertion portion, and a system including such an optical scanning endoscope.

Specifically, the system with the optical scanning endoscope is, for example, configured to scan an object in accordance with a preset scanning pattern by swinging a distal end portion of an illuminating fiber that guides illuminating light emitted from a light source section, receive return light from the object by light receiving fibers provided around the illuminating fiber, and generate an image of the object using signals obtained by resolving the return light received by the light receiving fibers into individual color components.

For example, a medical observation system described in Japanese Patent Application Laid-Open Publication No. 2011-19706 is conventionally known as the system having the above-described configuration.

Specifically, Japanese Patent Application Laid-Open Publication No. 2011-19706 discloses a medical observation system configured to, when a scanning medical probe substantially corresponding to the above-mentioned optical scanning endoscope is outside a patient, be able to control the amount of laser light emitted from a laser light source to the scanning medical probe.

SUMMARY OF THE INVENTION

An endoscope system according to an aspect of the present invention includes: a light transmitting section configured to transmit illuminating light generated by a light source and emit the light from a light exit surface; a light receiving section configured to receive return light of the light emitted from the light exit surface; a light guiding section configured to allow the light emitted from the light exit surface to be incident on the light receiving section by totally reflecting return light from a subject or the emitted light at least one or more times; a driving section configured to allow an end portion having the light exit surface of the light transmitting section to be swung to the subject during a first time period and to the light guiding section during a second time period so as to draw trajectories corresponding to predetermined scanning patterns; a light detecting section configured to detect, of the light emitted from the light exit surface of the light transmitting section, the return light from the subject during the first time period, as a signal for image generation, and the light received through the light guiding section during the second time period, as a signal for emission quality determination; a determination section configured to determine whether or not the pattern of fluctuations in a signal level detected by the light detecting section corresponds to a predetermined pattern of fluctuations; and a control section configured to, if a determination result is that the pattern of fluctuations in the signal level within the second time period does not correspond to the predetermined pattern of fluctuations, perform control for lowering a quantity of the illuminating light supplied by the light source to the light transmitting section, to zero or a predetermined value.

DETAILED DESCRIPTION OF THE PREFERRED EMBODIMENTS

Embodiments of the present invention will be described below with reference to the accompanying drawings.
(First Embodiment)

Figure 1:
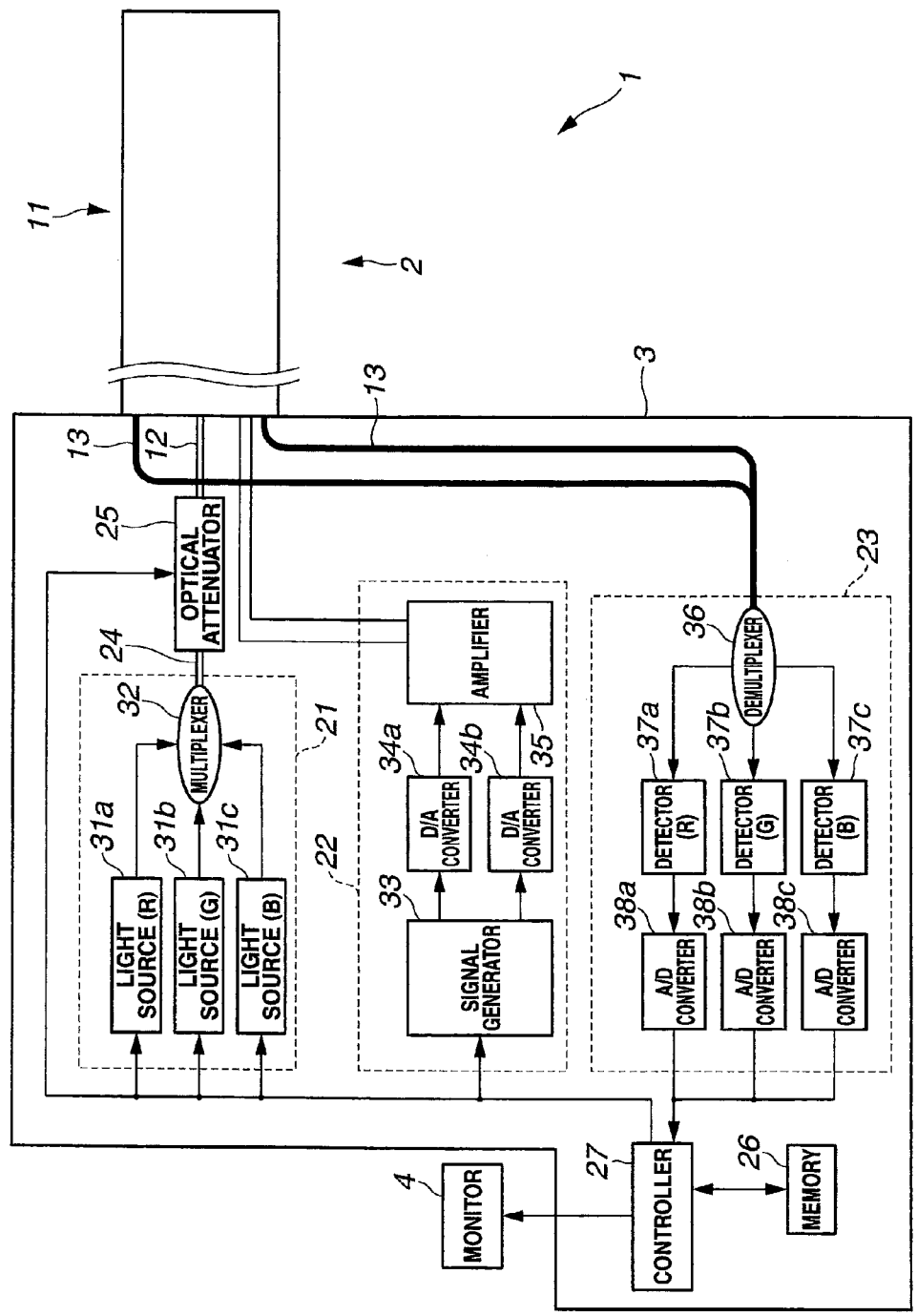
FIG. 1 illustrates a primary part configuration of an endoscope system according to an embodiment of the present invention.

FIGS. 1 through 13 are associated with a first embodiment of the present invention. FIG. 1 illustrates a primary part configuration of an endoscope system according to the embodiment of the present invention.

As shown in FIG. 1, for example, an endoscope system 1 includes a scanning endoscope 2 that can be inserted in the body cavity of a subject, an apparatus main body 3 connected to the endoscope 2, and a monitor 4 connected to the apparatus main body 3.

The endoscope 2 includes an elongated cylindrical and flexible insertion portion 11. Note that a proximal end portion of the insertion portion 11 is provided with a connector, not shown, for detachably connecting the endoscope 2 to the apparatus main body 3, or the like.

Figure 2:
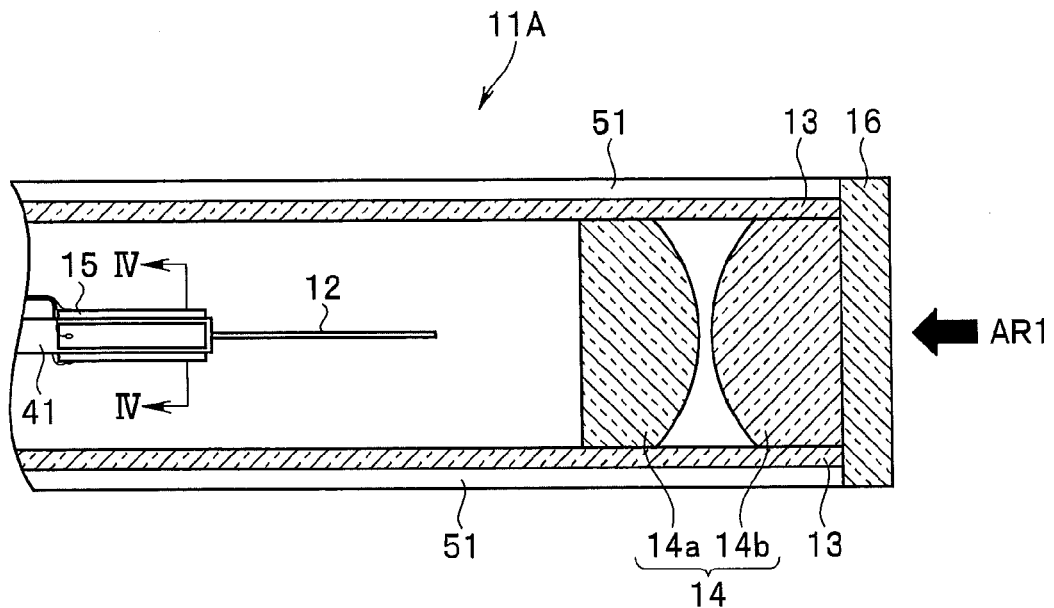
FIG. 2 is a schematic diagram illustrating an exemplary internal configuration of a distal end portion of the endoscope.

FIG. 2 is a schematic diagram illustrating an exemplary internal configuration of a distal end portion of the endoscope. As schematically illustrated in FIG. 2, the distal end portion 11A of the insertion portion 11 includes: a light exit end portion of an illuminating fiber 12 that functions as a light transmitting section for transmitting illuminating light supplied by the apparatus main body 3; a light incident end portion of light receiving fibers 13 that receive return light from an object and illuminating light through a light guiding plate 16 described later and guide these types of light to the apparatus main body 3; an objective optical system 14 that condenses the illuminating light emitted from the illuminating fiber 12 and emits the condensed light; and an actuator 15 that allows the light exit end portion of the illuminating fiber 12 to swing on the basis of a drive signal outputted from the apparatus main body 3. Each of the illuminating fiber 12, the objective optical system 14, and the actuator 15 is contained in a flexible sheath 51. Also, the multiple light receiving fibers 13 are annularly embedded in the sheath 51.

The objective optical system 14 includes a lens 14a through which illuminating light from the illuminating fiber 12 is received and a lens 14b through which the illuminating light from the lens 14a is emitted. The lenses 14a and 14b also each have positive refractive power.

Figure 3:
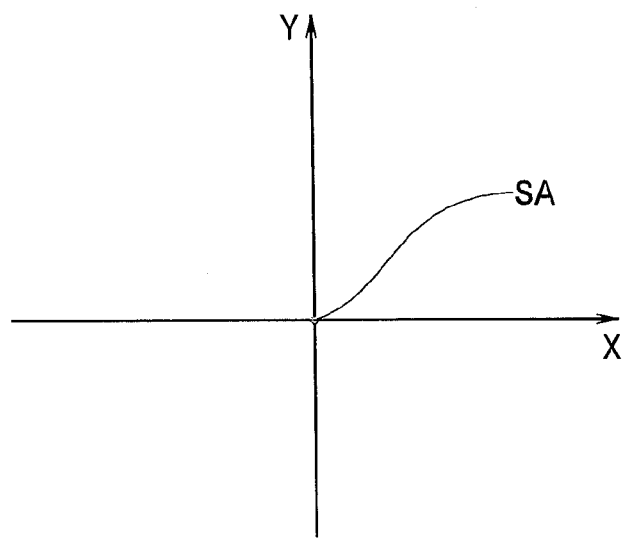
FIG. 3 illustrates an example of a virtual XY plane defined on a surface of an object.

Hereinafter, a description will be made with an example in which an XY plane as shown in FIG. 3 is defined on a surface of an object as a virtual plane orthogonal to an insertion axis (or an optical axis of the objective optical system 14) corresponding to a longitudinal axis of the insertion portion 11. FIG. 3 illustrates an example of the virtual XY plane defined on the surface of the object.

Specifically, if it is assumed that the insertion axis of the insertion portion 11 extends from the front to the depth of the drawing, a point SA on the XY plane in FIG. 3 is a point of intersection between the insertion axis and the drawing. An X axis direction on the XY plane in FIG. 3 defines a direction from the left to the right of the drawing. A Y axis direction on the XY plane in FIG. 3 defines a direction from the bottom to the top of the drawing. The X and Y axes on the XY plane in FIG. 3 intersect at the point SA.

Figure 4:
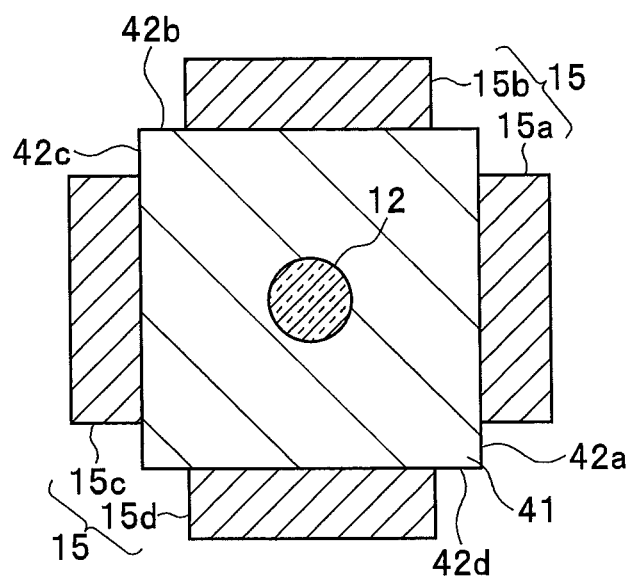
FIG. 4 is a cross-sectional view taken along line IV-IV in FIG. 2.

FIG. 4 is a cross-sectional view taken along line IV-IV in FIG. 2. As shown in FIG. 4, a ferrule 41, which is a joining member, is provided between the illuminating fiber 12 and the actuator 15. Specifically, the ferrule 41 is formed of zirconia (ceramic) or nickel, for example.

As shown in FIG. 4, the ferrule 41, which is formed as a quadratic prism, includes sides 42a and 42c orthogonal to the X axis direction, and sides 42b and 42d orthogonal to the Y axis direction. In addition, the illuminating fiber 12 is fixed at substantially the center of the ferrule 41. Note that the ferrule 41 may also be formed as any other prism.

As shown in FIG. 4, the actuator 15 includes an actuator 15a along the side 42a, an actuator 15b along the side 42b, an actuator 15c along the side 42c, and an actuator 15d along the side 42d.

The actuators 15a and 15c, each of which is formed of, for example, a piezoelectric element, are driven by a first drive signal outputted from a D/A converter 34a of a driver unit 22.

The actuators 15b and 15d, each of which is formed of, for example, a piezoelectric element, are driven by a second drive signal outputted from a D/A converter 34b of the driver unit 22.

A distal end face of the distal end portion 11A of the insertion portion 11 is covered with the light guiding plate 16, which is a transparent member being circular as viewed from a direction indicated by an arrow AR1, as schematically illustrated in FIG. 2.

The light guiding plate 16 has a predetermined refractive index distribution that is based on at least one of a refractive index of (the lens 14b of) the objective optical system 14 and a refractive index of air. Specifically, the light guiding plate 16, for example, has a predetermined refractive index distribution that allows illuminating light entering the light guiding plate 16 through the objective optical system 14 within a predetermined time period to be totally reflected one or more times (or odd-numbered times) into the light receiving fibers 13, allows illuminating light emitted from the illuminating fiber 12 through the objective optical system 14 out of the predetermined time period to be transmitted to an object, and allows return light of the illuminating light emitted to the object out of the predetermined time period to be transmitted into the light receiving fibers 13.

On the other hand, the apparatus main body 3 includes a light source unit 21, the driver unit 22, a detection unit 23, a light guide 24, an optical attenuator 25, memory 26, and a controller 27.

The light source unit 21 includes a light source 31a, a light source 31b, a light source 31c, and a multiplexer 32.

The light source 31a includes, for example, a light source that emits laser light, such as a laser or an SLD (super luminescent diode). The light source 31a is configured to emit light at a wavelength range of red (hereinafter, also referred to as R light) to the multiplexer 32 when being turned on in accordance with the control by the controller 27.

The light source 31b includes, for example, a light source that emits laser light, such as a laser or an SLD (super luminescent diode). The light source 31b is configured to emit light at a wavelength range of green (hereinafter, also referred to as G light) to the multiplexer 32 when being turned on in accordance with the control by the controller 27.

The light source 31c includes, for example, a light source that emits laser light, such as a laser or an SLD (super luminescent diode). The light source 31c is configured to emit light at a wavelength range of blue (hereinafter, also referred to as B light) to the multiplexer 32 when being turned on in accordance with the control by the controller 27.

The multiplexer 32 is configured to multiplex R light from the light source 31a, G light from the light source 31b, and B light from the light source 31c and supply the resultant light to the light guide 24.

The optical attenuator 25 is provided on an optical path for illuminating light emitted from the light guide 24 to a light incident end portion of the illuminating fiber 12 and is configured to allow the quantity of the illuminating light supplied to the illuminating fiber 12 to be adjusted by increasing or decreasing attenuation in accordance with the control by the controller 27.

The driver unit 22 includes a signal generator 33, digital-to-analog (hereinafter, referred to as D/A) converters 34a and 34b, and an amplifier 35.

Figure 5:
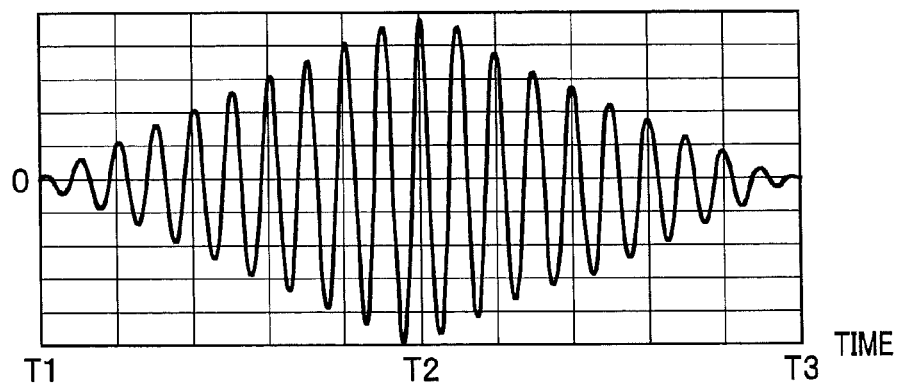
FIG. 5 illustrates an example signal waveform of a first drive signal supplied to an actuator provided in the endoscope.

The signal generator 33 is configured to, in accordance with the control by the controller 27, generate a signal having a predetermined waveform, for example, as shown in FIG. 5, as a first drive signal for swinging an end portion having a light exit surface of the illuminating fiber 12 in the X axis direction and output the first drive signal to the D/A converter 34a. FIG. 5 illustrates an example signal waveform of the first drive signal supplied to the actuator.

Figure 6:
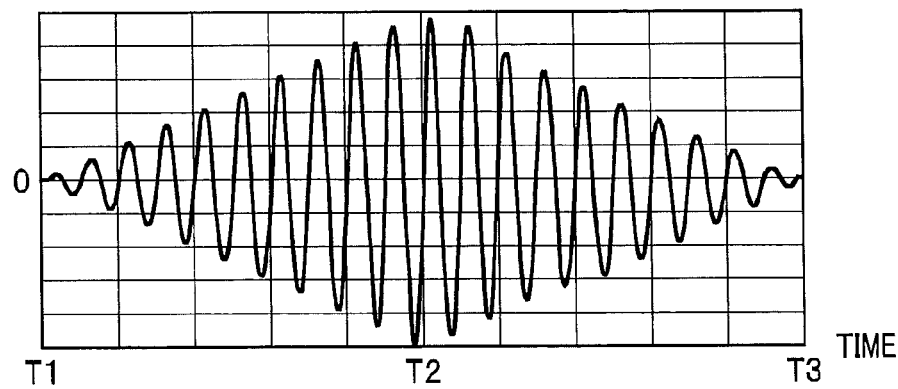
FIG. 6 illustrates an example signal waveform of a second drive signal supplied to the actuator provided in the endoscope.

The signal generator 33 is also configured to, in accordance with the control by the controller 27, generate a signal having a waveform, for example, as shown in FIG. 6, with a 90° phase shift from the first drive signal, as a second drive signal for swinging the end portion having the light exit surface of the illuminating fiber 12 in the Y axis direction and output the second drive signal to the D/A converter 34b. FIG. 6 illustrates an example signal waveform of the second drive signal supplied to the actuator.

The D/A converter 34a is configured to convert a digital first drive signal outputted from the signal generator 33 into an analog first drive signal and output the resultant signal to the amplifier 35.

The D/A converter 34b is configured to convert a digital second drive signal outputted from the signal generator 33 into an analog second drive signal and output the resultant signal to the amplifier 35.

The amplifier 35 is configured to amplify a first drive signal outputted from the D/A converter 34a and output the resultant signal to each of the actuators 15a and 15c. The amplifier 35 is also configured to amplify a second drive signal outputted from the D/A converter 34b and output the resultant signal to each of the actuators 15b and 15d.

An amplitude value (signal level) of the first drive signal as illustrated in FIG. 5 gradually increases from a minimum value at a time T1, reaches a maximum value at a time T2, then gradually decreases, and returns to the minimum value at a time T3.

An amplitude value (signal level) of the second drive signal as illustrated in FIG. 6 gradually increases from a minimum value at the time T1, reaches a maximum value at a time near the time T2, then gradually decreases, and returns to the minimum value at the time T3.

Figure 7A:
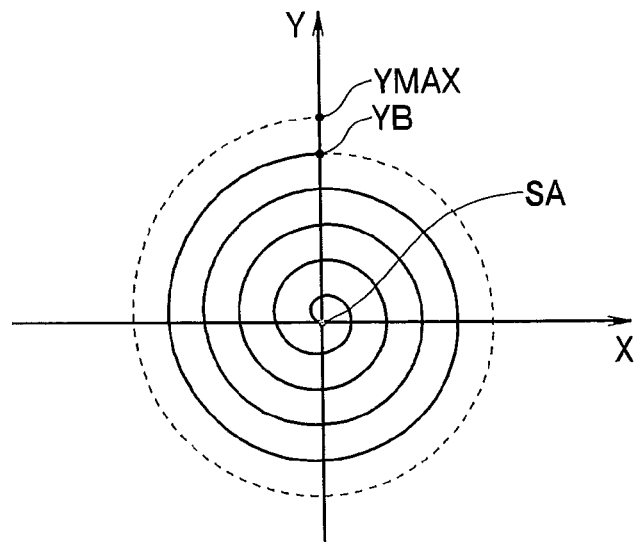
FIG. 7A illustrates a first spiral trajectory of illuminating light, the trajectory being drawn while the illuminating light is being applied to a virtual XY plane like FIG. 3 on a time-series basis.
Figure 7B:
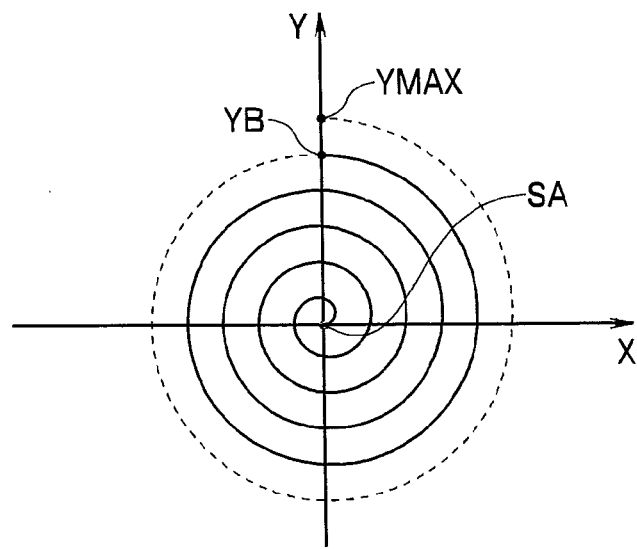
FIG. 7B illustrates a second spiral trajectory of illuminating light, the trajectory being drawn while the illuminating light is being applied to a virtual XY plane like FIG. 3 on a time-series basis.

Upon the supply of a first drive signal as shown in FIG. 5 to the actuators 15a and 15c and a second drive signal as shown in FIG. 6 to the actuators 15b and 15d, the end portion having the light exit surface of the illuminating fiber 12 is spirally swung from and around the point SA, and a surface of an object is spirally scanned in accordance with the swinging movement as shown in FIGS. 7A and 7B. FIG. 7A illustrates a first spiral trajectory of illuminating light, the trajectory being drawn while the illuminating light is being applied to a virtual XY plane like FIG. 3 on a time-series basis. FIG. 7B illustrates a second spiral trajectory of illuminating light, the trajectory being drawn while the illuminating light is being applied to a virtual XY plane like FIG. 3 on a time-series basis.

Specifically, at the time T1, illuminating light is applied to a position of the surface of the object corresponding to the point SA. Then, as the amplitude values of the first and second drive signals increase during the range from the time T1 to the time T2, the illuminated position on the surface of the object is moved in a manner that draws the first spiral trajectory from the point SA to a point YMAX, as shown in FIG. 7A. Then, as the amplitude values of the first and second drive signals decrease during the range from the time T2 to the time T3, the illuminated position on the surface of the object is moved in a manner that draws the second spiral trajectory from the point YMAX to the point SA, as shown in FIG. 7B. Finally, at the time T3, the illuminating light is applied to the point SA on the surface of the object.

However, according to the present embodiment, since the light guiding plate 16 having the above-described predetermined refractive index distribution covers the light exit surface of the objective optical system 14 (the lens 14b), no illuminating light is applied to a part on the surface of the object corresponding to the outermost circumference of the first and second spiral trajectories, whereas illuminating light is applied to a part on the surface of the object corresponding to the other first and second spiral trajectories than the outermost circumference.

Specifically, for example, no illuminating light is applied to each position on the surface of the object immediately after a point YB to the point YMAX, as drawn with dotted lines of the spiral trajectories in the FIGS. 7A and 7B, whereas illuminating light is applied to each position on the surface of the object from the point SA to the point YB, as drawn with solid lines of the spiral trajectories in the FIGS. 7A and 7B.

That is, the actuator 15 has the function of allowing the end portion having the light exit surface of the illuminating fiber 12 to be swung in accordance with spiral scanning patterns corresponding to the trajectories of the illuminated position as illustrated in FIGS. 7A and 7B on the basis of the first and second drive signals supplied by the driver unit 22.

The light guiding plate 16 of the present embodiment has a predetermined refractive index distribution that allows illuminating light entering the light guiding plate 16 through the objective optical system 14 within a predetermined time period NPA during which the illuminating fiber 12 is swung to the outermost circumference of the spiral scanning patterns described above (corresponding to the trajectories of the illuminated position as illustrated in FIGS. 7A and 7B), to be totally reflected one or more times (or odd-numbered times) into the light receiving fibers 13, allows illuminating light emitted from the illuminating fiber 12 through the objective optical system 14 out of the predetermined time period NPA to be transmitted to an object, and allows return light of the illuminating light emitted to the object out of the predetermined time period NPA to be transmitted into the light receiving fibers 13.

On the other hand, the detection unit 23 includes a demultiplexer 36, detectors 37a, 37b, and 37c, and analog-to-digital (hereinafter, referred to as A/D) converters 38a, 38b, and 38c.

The demultiplexer 36, which includes a dichroic mirror and the like, is configured to demultiplex light emitted from a light exit surface of the light receiving fibers 13 into individual color components, i.e., R (red), G (green), and B (blue) and emit these color components to the detectors 37a, 37b, and 37c, respectively.

The detector 37a is configured to detect the intensity of R light outputted from the demultiplexer 36, generate an analog R signal corresponding to the detected intensity of the R light, and output the resultant signal to the A/D converter 38a.

The detector 37b is configured to detect the intensity of G light outputted from the demultiplexer 36, generate an analog G signal corresponding to the detected intensity of the G light, and output the resultant signal to the A/D converter 38b.

The detector 37c is configured to detect the intensity of B light outputted from the demultiplexer 36, generate an analog B signal corresponding to the detected intensity of the B light, and output the resultant signal to the A/D converter 38c.

The A/D converter 38a is configured to convert the analog R signal outputted from the detector 37a into a digital R signal and output the resultant signal to the controller 27.

The A/D converter 38b is configured to convert the analog G signal outputted from the detector 37b into a digital G signal and output the resultant signal to the controller 27.

The A/D converter 38c is configured to convert the analog B signal outputted from the detector 37c into a digital B signal and output the resultant signal to the controller 27.

The memory 26 stores a control program for the control of each component of the apparatus main body 3 and the like in advance and also pre-stores information that can be used to determine the emission quality of illuminating light from the illuminating fiber 12.

The controller 27 is configured to read the control program stored in the memory 26 and control the light source unit 21 and the driver unit 22 on the basis of the read control program.

The controller 27 is configured to generate an image for one frame on the basis of R, G, and B signals outputted from the detection unit 23 within a time period that does not overlap the predetermined time period NPA between the time T1 and the time T2 and allow the generated image to be displayed on the monitor 4.

The controller 27 is also configured to generate an image for one frame on the basis of R, G, and B signals outputted from the detection unit 23 within a time period that does not overlap the predetermined time period NPA between the time T2 and the time T3 and allow the generated image to be displayed on the monitor 4.

Furthermore, the controller 27 is configured to determine the emission quality of the illuminating light emitted from the illuminating fiber 12 on the basis of the information stored in the memory 26 and R, G, and B signals outputted from the detection unit 23 within the predetermined time period NPA and control the light source unit 21 and/or the optical attenuator 25 depending on the determined results. Note that the details of such determination processing and control will be described later.

That is, in the present embodiment, R, G, and B signals outputted from the detection unit 23 within the predetermined time period NPA are used only to determine the emission quality of the illuminating light emitted from the illuminating fiber 12. Thus, in the present embodiment, the monitor 4 will display an image corresponding to return light incident on the light receiving fibers 13 from individual positions between the point SA and the point YB on the surface of the object, as indicated by the solid lines of the spiral trajectories shown in FIGS. 7A and 7B.

Next, the operation of the endoscope system 1 having the above-mentioned configuration will be described.

Upon power-on of each component of the endoscope system 1, the controller 27 controls the light source unit 21 such that the light sources 31a, 31b, and 31c each emit a predetermined quantity of illuminating light, controls the driver unit 22 to output the first and second drive signals to the actuator 15, and controls the optical attenuator 25 such that the attenuation of the attenuator changes to zero. Alternatively, upon power-on of each component of the endoscope system 1, the controller 27 controls the light source unit 21 such that the light sources 31a, 31b, and 31c each emit a maximum quantity of illuminating light, controls the driver unit 22 to output the first and second drive signals to the actuator 15, and controls the optical attenuator 25 such that the attenuation of the attenuator changes to a predetermined attenuation DB other than zero. As a result of such control by the controller 27, the end portion having the light exit surface of the illuminating fiber 12 is swung and mixed light of R, G, and B light is emitted from the illuminating fiber 12 as illuminating light.

Then, the controller 27 causes an image generated on the basis of R, G, and B signals outputted from the detection unit 23 out of the predetermined time period NPA to be displayed on the monitor 4, while determining the emission quality of the illuminating light from the illuminating fiber 12 by performing the processing described below on the basis of the information stored in the memory 26 and R, G, and B signals outputted from the detection unit 23 within the predetermined time period NPA.

Figure 8:
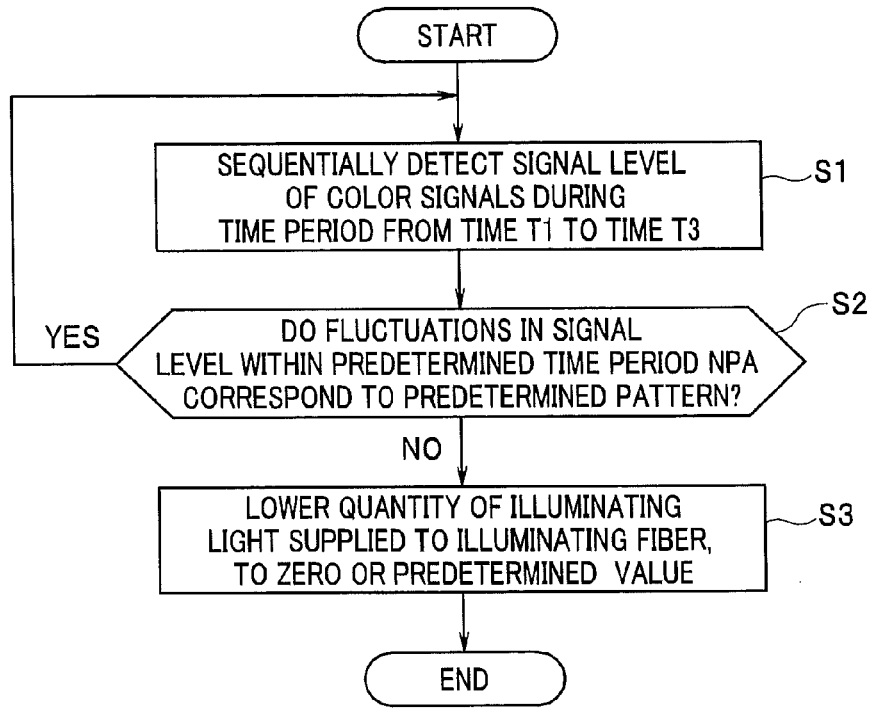
FIG. 8 is a flowchart showing exemplary processing performed by the endoscope system according to each embodiment of the present invention.

Now, a specific example of the processing performed for the determination of the emission quality of the illuminating light from the illuminating fiber 12 will be described. FIG. 8 is a flowchart showing exemplary processing performed by the endoscope system according to each embodiment of the present invention.

First, the controller 27 sequentially detects a color signal level of at least one of the R, G, and B signals outputted from the detection unit 23 during the time period between the time T1 and the time T3 (step S1 of FIG. 8).

Next, the controller 27, which has the function of a determination section, determines whether or not fluctuations in the signal level within the predetermined time period NPA correspond to a predetermined pattern, on the basis of the detection results of the signal level in step S1 of FIG. 8 and the information stored in the memory 26 (step S2 of FIG. 8).

Figure 9:
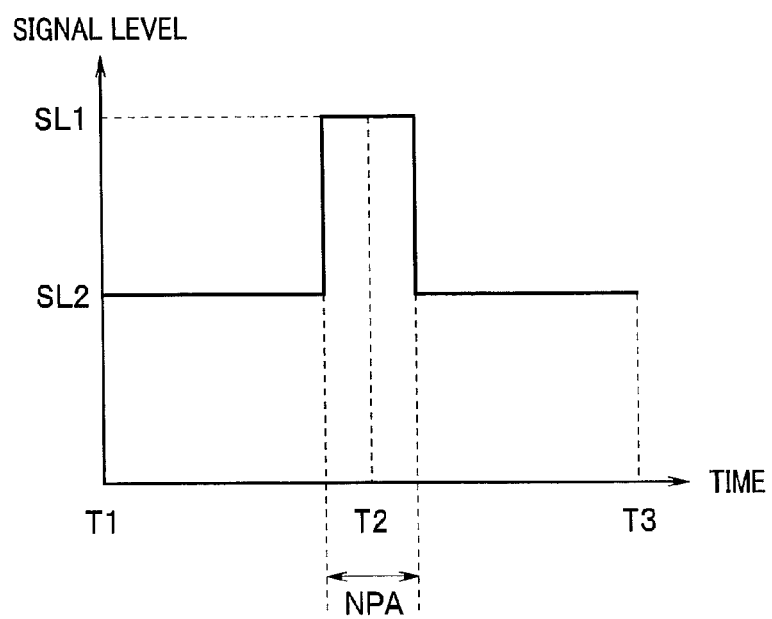
FIG. 9 illustrates an example pattern of fluctuations in a signal level detected while illuminating light is properly emitted.

Specifically, for example, once reading the information on a pattern of fluctuations in a signal level as shown in FIG. 9 from the memory 26, the controller 27 determines whether or not the fluctuations in the signal level within the predetermined time period NPA included in the detection results of the signal level obtained in step S1 of FIG. 8 correspond to the pattern of the fluctuations in the signal level included in the information read from the memory 26. FIG. 9 illustrates an example pattern of fluctuations in a signal level detected while illuminating light is properly emitted.

The pattern of fluctuations in a signal level illustrated in FIG. 9 is obtained as a result of the swinging movement of the trajectories along the spiral scanning patterns (as illustrated in FIGS. 7A and 7B) with illuminating light being emitted from the illuminating fiber 12, and represents a pattern of fluctuations substantially corresponding to a rectangular wave in which a signal level SL1 within the predetermined time period NPA is always higher than a signal level SL2 out of the predetermined time period NPA.

That is, the memory 26 of the present embodiment prestores the information on the pattern of the fluctuations in the signal level obtained if illuminating light emitted in accordance with the predetermined scanning pattern is proper.

Note that the signal level SL1 indicates a signal level detected during the predetermined time period NPA if illuminating light is properly emitted from the illuminating fiber 12, while the signal level SL2 indicates a signal level detected out of the predetermined time period NPA if illuminating light is properly emitted from the illuminating fiber 12.

In step S2 of FIG. 8, if the controller 27 determines that the fluctuations in the signal level within the predetermined time period NPA included in the detection results of the signal level obtained in step S1 of FIG. 8 correspond to the pattern of the fluctuations included in the information read from the memory 26, then the controller 27 assumes that the illuminating light is properly emitted from the illuminating fiber 12 and returns the processing to step S1 of FIG. 8 while continuing the control for supplying the illuminating fiber 12 with illuminating light.

By contrast, in step S2 of FIG. 8, if the controller 27 determines that the fluctuations in the signal level within the predetermined time period NPA included in the detection results of the signal level obtained in step S1 of FIG. 8 do not correspond to the pattern of the fluctuations included in the information read from the memory 26, then the controller 27 assumes that an anomaly has occurred in the illuminating light emitted from the illuminating fiber 12 and carries out the control for lowering the quantity of illuminating light supplied by the light source unit 21 to the illuminating fiber 12, to zero or a predetermined value (step S3 of FIG. 8).

Figure 10:
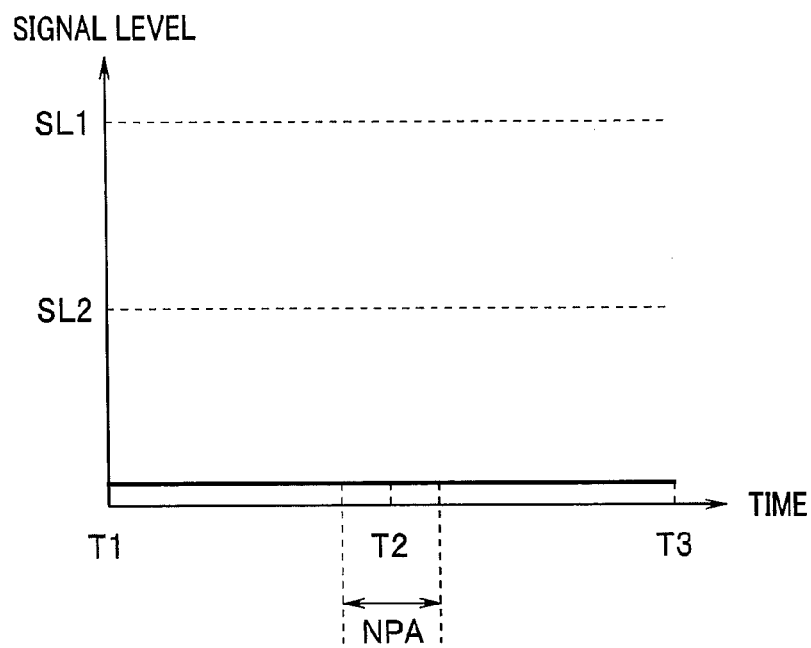
FIG. 10 illustrates an example pattern of fluctuations in a signal level detected if the emission quality of the illuminating light is improper.
Figure 11:
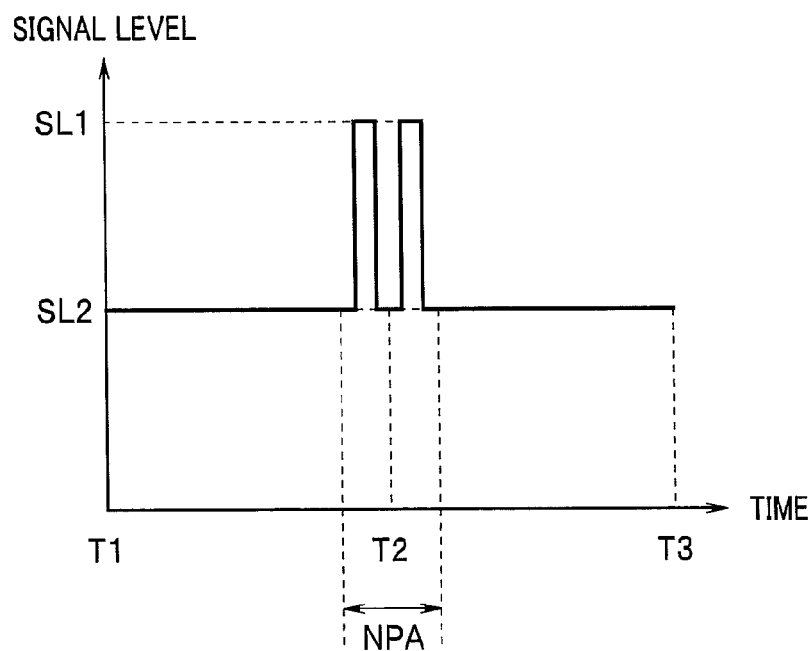
FIG. 11 illustrates another example pattern of fluctuations in a signal level detected if the emission quality of the illuminating light is improper, the pattern being different from that shown in FIG. 10.

Specifically, if the fluctuations in the signal level within the predetermined time period NPA included in the detection results of the signal level obtained in step S1 of FIG. 8 represent a pattern shown in, for example, FIG. 10 or 11, then the controller 27 assumes that an anomaly has occurred in the illuminating light emitted from the illuminating fiber 12. FIG. 10 illustrates an example pattern of fluctuations in a signal level detected if the emission quality of the illuminating light is improper. FIG. 11 illustrates another example pattern of fluctuations in a signal level detected if the emission quality of the illuminating light is improper, the pattern being different from that shown in FIG. 10.

The pattern of fluctuations in a signal level illustrated in FIG. 10, which is obtained if, for example, the illuminating fiber 12 is bent, represents a pattern in which both the signal levels within and out of the predetermined time period NPA are evenly close to zero.

The pattern of fluctuations in a signal level illustrated in FIG. 11 is due to, for example, an anomaly in the operation of at least one of the actuators 15a to 15d, and is obtained in the event of the swinging movement deviating from the trajectories corresponding to the spiral scanning patterns (as illustrated in FIGS. 7A and 7B) with illuminating light being emitted from the illuminating fiber 12. In this pattern, the predetermined time period NPA includes the detection timing of both the signal levels SL1 and SL2.

On the other hand, the controller 27 lowers the quantity of illuminating light for the illuminating fiber 12 to zero by, for example, the control for turning the light sources 31a, 31b, and 31c off. Alternatively, the controller 27 lowers the quantity of illuminating light for the illuminating fiber 12 to a predetermined value by, for example, the control for increasing the attenuation of illuminating light at the optical attenuator 25 from zero or the predetermined attenuation DB.

Note that the predetermined value is set at a quantity of light that ensures body safety even if illuminating light continues to be emitted with the actuator 15 stopping the swinging movement of the illuminating fiber 12. Specifically, the predetermined value is set at a quantity of light that, for example, keeps the level of signals outputted from the detection unit 23 being equal to or under 1 mW at any time.

According to the present embodiment hereinbefore described, a series of processes as shown in FIG. 8, which can be performed during the operation of the endoscope system 1, allow the quantity of illuminating light for the illuminating fiber 12 to be quickly lowered to the quantity of light that ensures the safety of a body in the event of an anomaly occurring in the illuminating light emitted from the illuminating fiber 12. This can reduce the risk of an adverse effect on the body caused by the illuminating light used for scanning an object.

Also, according to the present embodiment, the light receiving fibers 13 can receive light used for generating an image to be displayed on the monitor 4 (i.e., return light from an object) and light used for determining the emission quality of illuminating light from the illuminating fiber 12. As a result, according to the present embodiment, a configuration can be achieved that determines the emission quality of the illuminating light from the illuminating fiber 12 with the thickness in diameter of the insertion portion 11 being substantially left unchanged from that of a conventional insertion portion.

Figure 12:
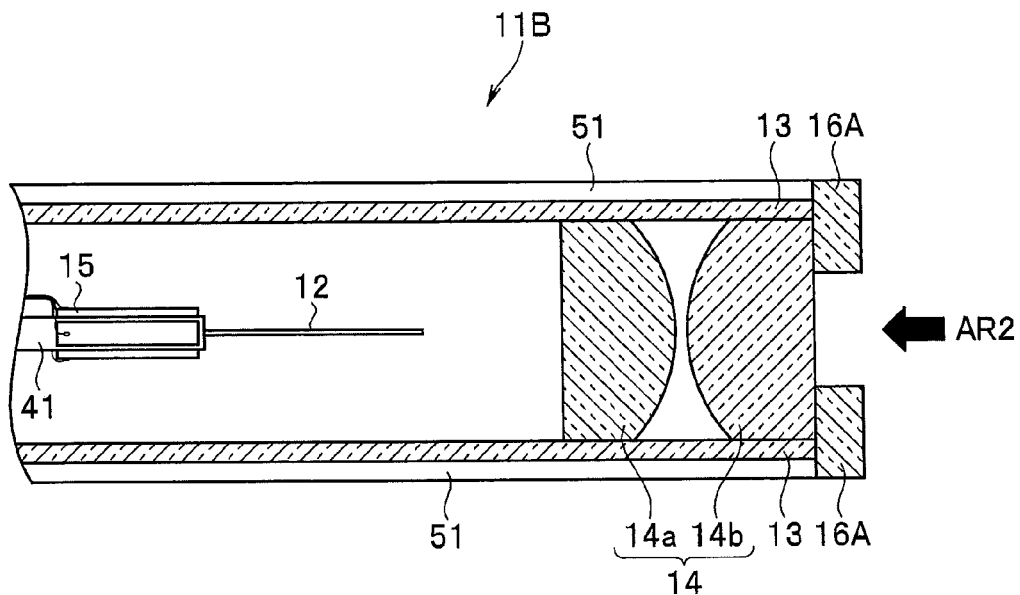
FIG. 12 is a schematic diagram illustrating another exemplary internal configuration of the distal end portion of the endoscope, the internal configuration being different from that illustrated in FIG. 2.
Figure 13:
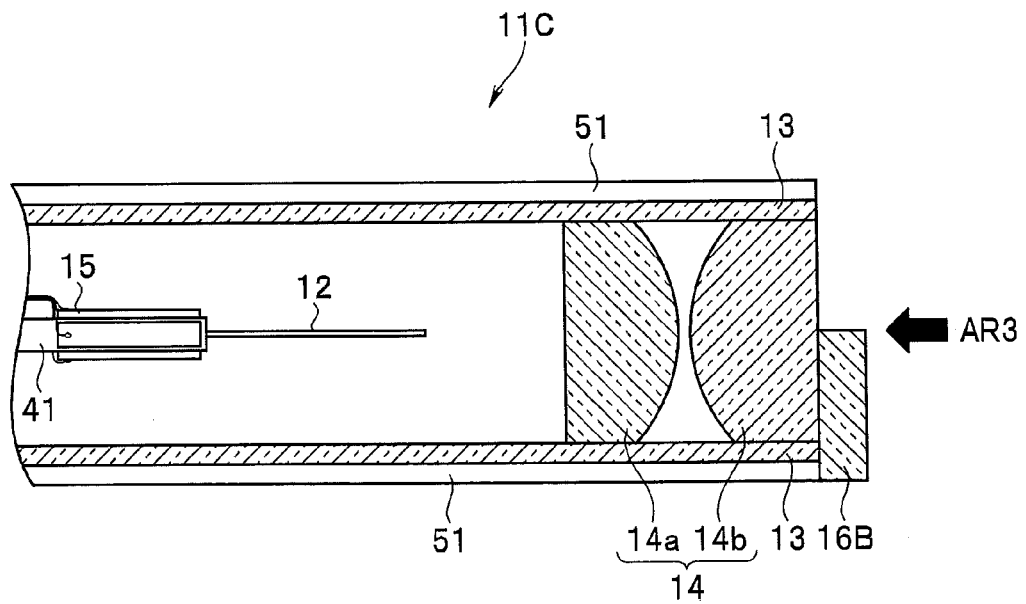
FIG. 13 is a schematic diagram illustrating yet another exemplary internal configuration of the distal end portion of the endoscope, the internal configuration being different from those illustrated in FIGS. 2 and 12.

Note that according to the present embodiment, any other non-circular light guiding plate may also be provided on the distal end face of the distal end portion of the insertion portion 11 as long as the light guiding plate has a refractive index distribution that meets the same condition as that of the light guiding plate 16 (the condition that illuminating light entering the light guiding plate through the objective optical system 14 within the predetermined time period NPA, during which the illuminating fiber 12 is swung to the outermost circumference of the spiral scanning patterns, is allowed to be totally reflected one or more times into the light receiving fibers 13). FIG. 12 is a schematic diagram illustrating another exemplary internal configuration of the distal end portion of the endoscope, the internal configuration being different from that illustrated in FIG. 2. FIG. 13 is a schematic diagram illustrating yet another exemplary internal configuration of the distal end portion of the endoscope, the internal configuration being different from those illustrated in FIGS. 2 and 12.

Specifically, for example, as schematically illustrated in FIG. 12, a distal end face of a distal end portion 11B of the insertion portion 11 may also be covered with a light guiding plate 16A that has a refractive index distribution meeting the same condition as that of the light guiding plate 16 and is a transparent member having an annular ring shape as viewed from a direction indicated by an arrow AR2.

Alternatively, for example, as schematically illustrated in FIG. 13, a distal end face of a distal end portion 11C of the insertion portion 11 may also be covered with a light guiding plate 16B that has a refractive index distribution meeting the same condition as that of the light guiding plate 16 and is a transparent member having a fan shape as viewed from a direction indicated by an arrow AR3.

(Second Embodiment)

Figure 14:
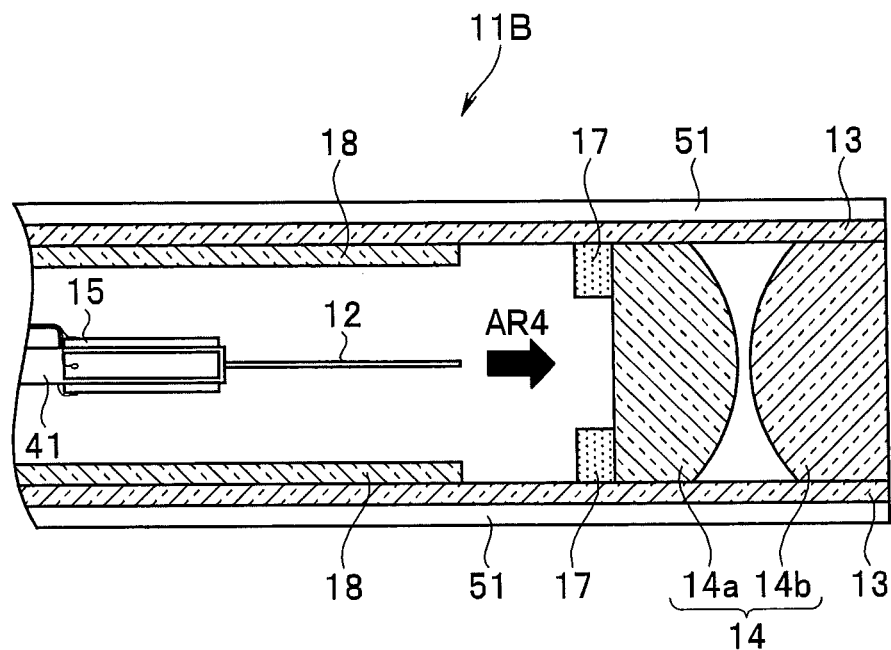
FIG. 14 is a schematic diagram illustrating still another exemplary internal configuration of the distal end portion of the endoscope, the internal configuration being different from those illustrated in FIGS. 2, 12, and 13.

FIG. 14 is associated with a second embodiment of the present invention.

Note that in the present embodiment, detailed descriptions of the same components as those in the first embodiment will be omitted, while components that are not seen in the first embodiment will be mainly described.

An insertion portion 11 of the present embodiment has a distal end portion 11D as shown in FIG. 14, instead of the distal end portions 11A to 11C described in the first embodiment. FIG. 14 is a schematic diagram illustrating still another exemplary internal configuration of the distal end portion of the endoscope, the internal configuration being different from those illustrated in FIGS. 2, 12, and 13.

Specifically, as schematically illustrated in FIG. 14, the distal end portion 11D of the insertion portion 11 includes a light exit end portion of an illuminating fiber 12, a light incident end portion of light receiving fibers 13, an objective optical system 14, an actuator 15, and a reflection member 17 and a plurality of monitoring fibers 18 contained in a sheath 51.

The reflection member 17 is formed of a reflection mirror, a reflection coating, or metal and the like and is positioned so as to allow illuminating light emitted from the illuminating fiber 12 within the predetermined time period NPA, during which the illuminating fiber 12 is swung to the outermost circumference of the above-described spiral scanning patterns (corresponding to the trajectories of the illuminated positions as illustrated in FIGS. 7A and 7B), to enter the monitoring fibers 18.

Specifically, for example, as schematically illustrated in FIG. 14, the reflection member 17 is provided so as to cover a region corresponding to an outermost part of a light incident plane of a lens 14a in a manner that the reflection member 17 has an annular ring shape as viewed from a direction indicated by an arrow AR4.

The plurality of monitoring fibers 18 are annularly arranged and fixed such that their light incident planes are disposed at respective positions that face the reflection member 17.

Note that, although not shown, the monitoring fibers 18 are joined together with the light receiving fibers 13 near a proximal end portion of the insertion portion 11, for example. Thus, illuminating light received by the monitoring fibers 18 travels through substantially the same path as the light receiving fibers 13 into a demultiplexer 36 of a detection unit 23.

Also in the configuration with the insertion portion 11 having the distal end portion 11D, the series of processes as shown in FIG. 8 can be applied in substantially the same manner. Thus, according to the present embodiment, the quantity of illuminating light for the illuminating fiber 12 can be quickly lowered to a quantity of light that ensures the safety of a body in the event of an anomaly occurring in the illuminating light emitted from the illuminating fiber 12. This can reduce the risk of an adverse effect on the body caused by the illuminating light used for scanning an object.

Also, according to the present embodiment, the light receiving fibers 13 can receive light used for generating an image to be displayed on the monitor 4 (i.e., return light from an object) as well as the monitoring fibers 18 can receive light used for determining the emission quality of the illuminating light from the illuminating fiber 12. As a result, according to the present embodiment, a configuration can be achieved that determines the emission quality of the illuminating light from the illuminating fiber 12 with the quality of an image to be displayed on the monitor 4 being substantially left unchanged from that of a conventional image.

Note that according to the present embodiment, the arrangement of the reflection member 17 and the monitoring fibers 18 is not limited to an annular ring shape. For example, the monitoring fibers 18 may also be provided at four positions corresponding to actuators 15a to 15d in the X axis and Y axis directions, and only parts of the light incident plane of the lens 14a that face the light incident planes of the monitoring fibers 18 may be covered with the reflection member 17.

(Third Embodiment)

Figure 15:
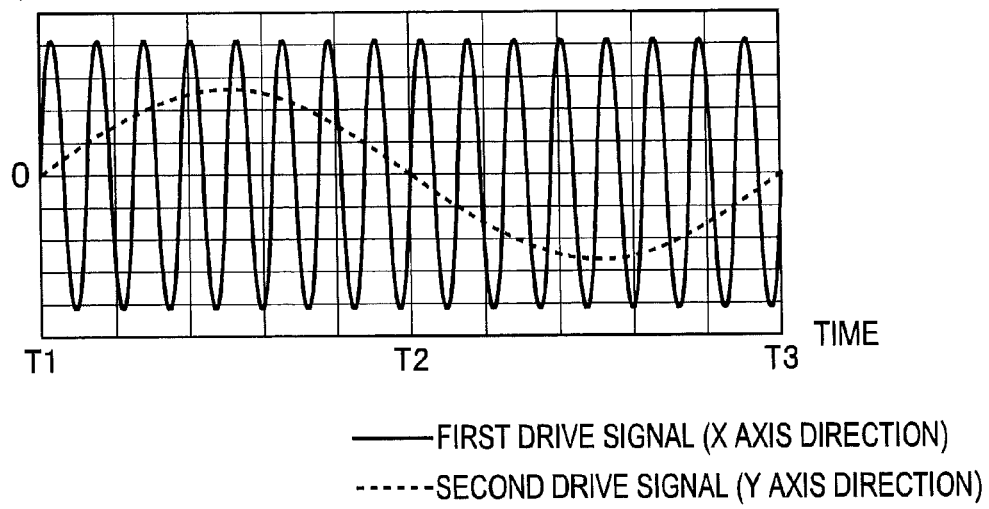
FIG. 15 illustrates another example signal waveform of a drive signal supplied to the actuator provided in the endoscope, the signal waveform being different from those illustrated in FIGS. 5 and 6.
Figure 16:
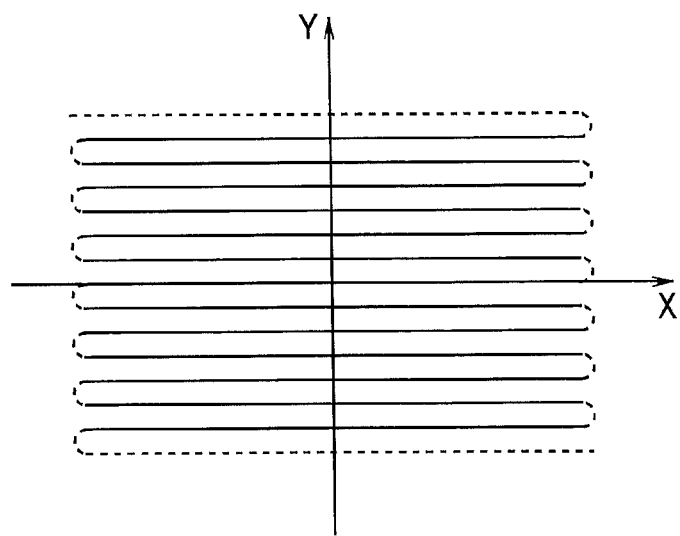
FIG. 16 illustrates a raster trajectory of illuminating light, the trajectory being drawn while the illuminating light is being applied to a virtual XY plane like FIG. 3 on a time-series basis.

FIGS. 15 and 16 are associated with a third embodiment of the present invention.

Note that in the present embodiment, detailed descriptions of the same components as those in the first and second embodiments will be omitted, while components that are not seen in the first and second embodiments will be mainly described.

An illuminating fiber 12 of the present embodiment is configured to be swung in response to the operation of an actuator 15 in accordance with a raster scanning pattern, rather than the spiral scanning pattern described in the first embodiment. FIG. 15 illustrates another example signal waveform of a drive signal supplied to the actuator provided in the endoscope, the signal waveform being different from those illustrated in FIGS. 5 and 6. FIG. 16 illustrates a raster trajectory of illuminating light, the trajectory being drawn while the illuminating light is being applied to a virtual XY plane like FIG. 3 on a time-series basis.

Specifically, a driver unit 22 of the present embodiment is configured to generate a first drive signal and a second drive signal, for example, each having a waveform shown in FIG. 15 and supply the actuator 15 with the generated signals.

Also, a light guiding plate 16 of the present embodiment has a predetermined refractive index distribution that allows illuminating light entering the light guiding plate 16 through an objective optical system 14 within a predetermined time period NPB during which the illuminating fiber 12 is swung to outermost segments of the raster scanning pattern (dotted line segments of the trajectory shown in FIG. 16), to be totally reflected one or more times (or odd-numbered times) into light receiving fibers 13, allows illuminating light emitted from the illuminating fiber 12 through the objective optical system 14 out of the predetermined time period NPB to be transmitted to an object, and allows return light of the illuminating light emitted to the object out of the predetermined time period NPB to be transmitted into the light receiving fibers 13.

A controller 27 of the present embodiment is configured to determine whether or not fluctuations in the signal level within the predetermined time period NPB correspond to a predetermined pattern, on the basis of the detection results of the signal level obtained in substantially the same process as step S1 of FIG. 8 and information stored in memory 26. Furthermore, the controller 27 is configured to allow the control of lowering the quantity of illuminating light for the illuminating fiber 12 to be performed if the fluctuations in the signal level within the predetermined time period NPB do not correspond to the predetermined pattern.

Thus, according to the present embodiment, the quantity of illuminating light supplied to the illuminating fiber 12 can be quickly lowered to a quantity of light that ensures the safety of a body in the event of an anomaly occurring in the illuminating light emitted from the illuminating fiber 12. This can reduce the risk of an adverse effect on the body caused by the illuminating light used for scanning an object.

(Fourth Embodiment)

Figure 17:
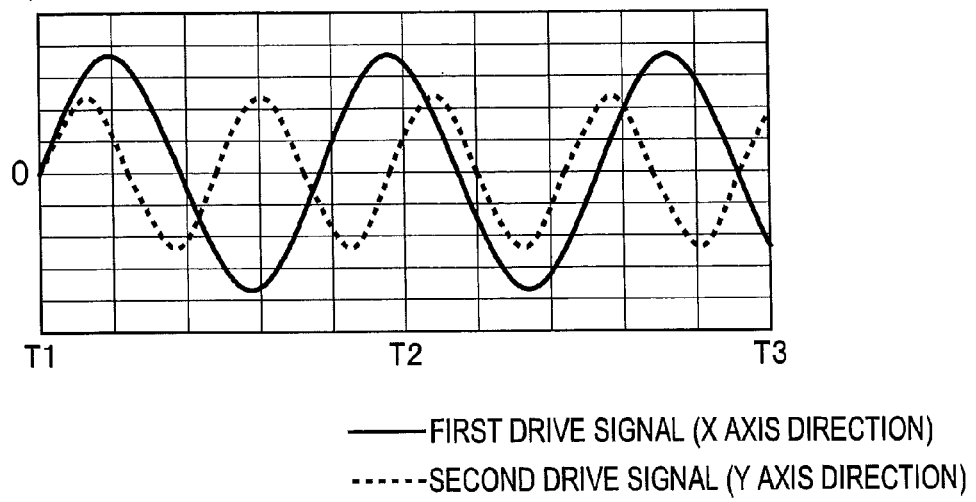
FIG. 17 illustrates yet another example signal waveform of a drive signal supplied to the actuator provided in the endoscope, the signal waveform being different from those illustrated in FIGS. 5, 6, and 15.
Figure 18:
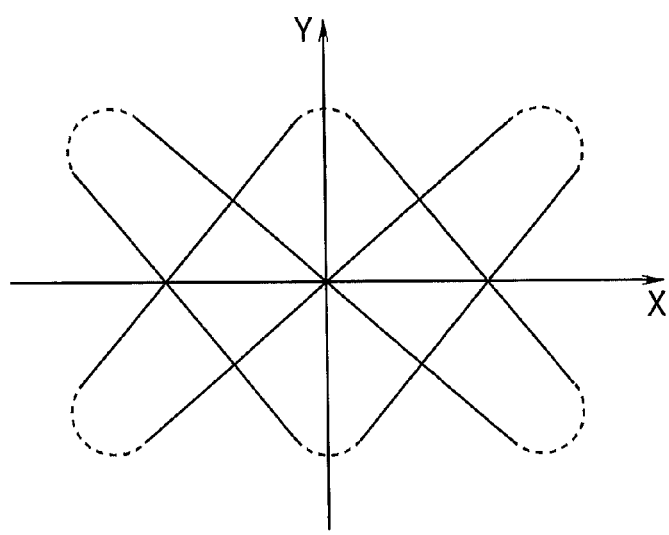
FIG. 18 illustrates a Lissajous trajectory of illuminating light, the trajectory being drawn while the illuminating light is being applied to a virtual XY plane like FIG. 3 on a time-series basis.

FIGS. 17 through 18 are associated with a fourth embodiment of the present invention.

Note that in the present embodiment, detailed descriptions of the same components as those in the first to third embodiments will be omitted, while components that are not seen in the first to third embodiments will be mainly described.

An illuminating fiber 12 of the present embodiment is configured to be swung in response to the operation of an actuator 15 in accordance with a Lissajous scanning pattern, rather than the spiral scanning pattern described in the first embodiment or the raster scanning pattern described in the third embodiment. FIG. 17 illustrates yet another example signal waveform of a drive signal supplied to the actuator provided in the endoscope, the signal waveform being different from those illustrated in FIGS. 5, 6, and 15. FIG. 18 illustrates a Lissajous trajectory of illuminating light, the trajectory being drawn while the illuminating light is being applied to a virtual XY plane like FIG. 3 on a time-series basis.

Specifically, a driver unit 22 of the present embodiment is configured to generate a first drive signal and a second drive signal, for example, each having a waveform as shown in FIG. 17 and supply the actuator 15 with the generated signals.

Also, a light guiding plate 16 of the present embodiment has a predetermined refractive index distribution that allows illuminating light entering the light guiding plate 16 through an objective optical system 14 within a predetermined time period NPC during which the illuminating fiber 12 is swung to outermost segments of the Lissajous scanning pattern (dotted line segments of the trajectory shown in FIG. 18), to be totally reflected one or more times (or odd-numbered times) into light receiving fibers 13, allows illuminating light emitted from the illuminating fiber 12 through the objective optical system 14 out of the predetermined time period NPC to be transmitted to an object, and allows return light of the illuminating light emitted to the object out of the predetermined time period NPC to be transmitted into the light receiving fibers 13.

In addition, a controller 27 of the present embodiment is configured to determine whether or not fluctuations in the signal level within the predetermined time period NPC correspond to a predetermined pattern, on the basis of the detection results of the signal level obtained in substantially the same process as step S1 of FIG. 8 and information stored in memory 26. Furthermore, the controller 27 is configured to allow the control of lowering the quantity of illuminating light for the illuminating fiber 12 to be performed if the fluctuations in the signal level within the predetermined time period NPC do not correspond to the predetermined pattern.

Thus, according to the present embodiment, the quantity of illuminating light supplied to the illuminating fiber 12 can be quickly lowered to a quantity of light that ensures the safety of a body in the event of an anomaly occurring in the illuminating light emitted from the illuminating fiber 12. This can reduce the risk of an adverse effect on the body caused by the illuminating light used for scanning an object.

(Fifth Embodiment)

Figure 19:
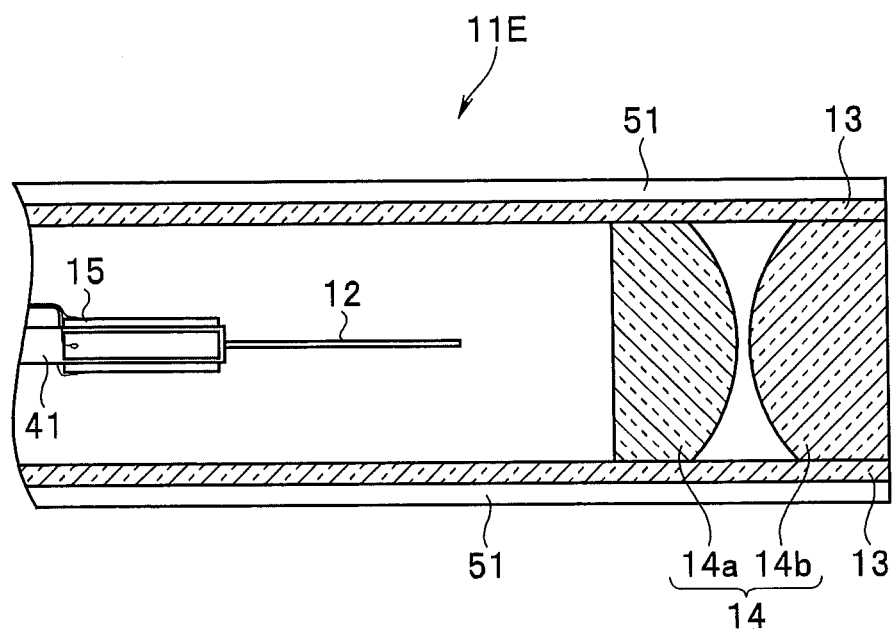
FIG. 19 is a schematic diagram illustrating still another exemplary internal configuration of the distal end portion of the endoscope, the internal configuration being different from those illustrated in FIGS. 2, 12, 13, and 14.
Figure 20:
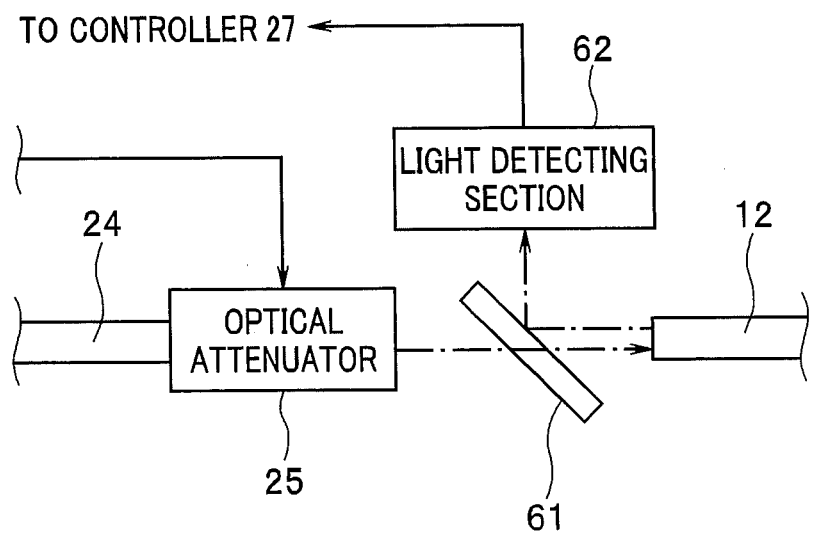
FIG. 20 illustrates an exemplary configuration for detecting return light emitted from an illuminating fiber.
Figure 21:
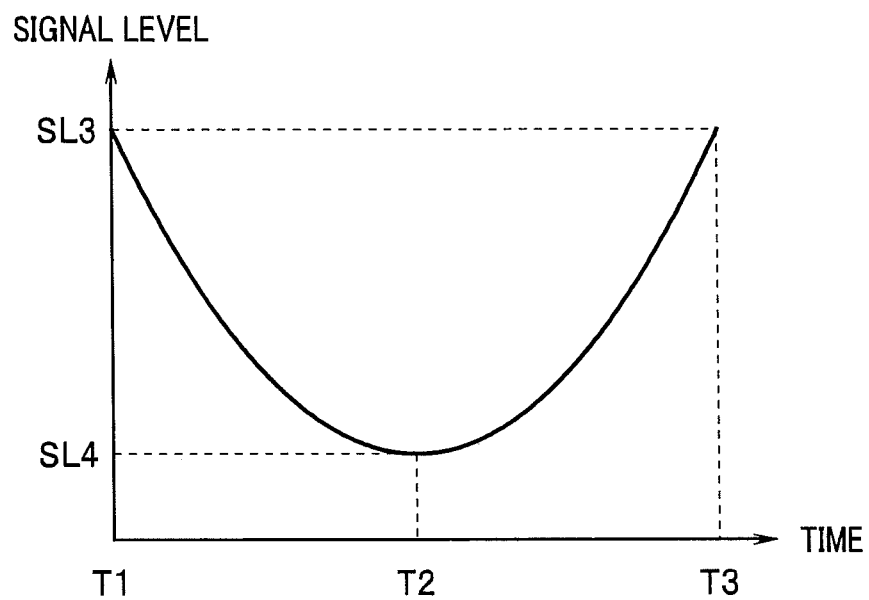
FIG. 21 illustrates another example pattern of fluctuations in a signal level detected while illuminating light is properly emitted, the pattern being different from that illustrated in FIG. 9.

FIGS. 19 through 21 are associated with a fifth embodiment of the present invention.

Note that in the present embodiment, detailed descriptions of the same components as those in the first to fourth embodiments will be omitted, while components that are not seen in the first to fourth embodiments will be mainly described.

An insertion portion 11 of the present embodiment has a distal end portion 11E as shown in FIG. 19, instead of the distal end portions 11A to 11D described in the first and second embodiments. FIG. 19 is a schematic diagram illustrating still another exemplary internal configuration of the distal end portion of the endoscope, the internal configuration being different from those illustrated in FIGS. 2, 12, 13, and 14.

Specifically, as schematically illustrated in FIG. 19, the distal end portion 11E of the insertion portion 11 includes an illuminating fiber 12, an objective optical system 14, and an actuator 15 that are contained in a sheath 51, and a plurality of light receiving fibers 13 annularly embedded in the sheath 51. That is, the distal end portion 11E of the insertion portion 11 is similar to the distal end portion 11A of the first embodiment except that the distal end portion 11E has no light guiding plate 16.

On the other hand, an apparatus main body 3 of the present embodiment is configured to allow the detection of return light generated when the light exit surface of the illuminating fiber 12 and the light exit surface of the lens 14b reflect the illuminating light transmitted by the illuminating fiber 12. FIG. 20 illustrates an exemplary configuration for detecting return light emitted from the illuminating fiber.

Specifically, for example, as illustrated in FIG. 20, the apparatus main body 3 of the present embodiment includes an optical member 61 provided on an optical path extending from an optical attenuator 25 to a light incident plane of the illuminating fiber 12 and a light detecting section 62 that receives return light from the optical member 61.

The optical member 61 is made of, for example, a glass plate provided diagonally to the optical axis of illuminating light emitted from the optical attenuator 25. The optical member 61 has the function of allowing the transmission of illuminating light emitted from the optical attenuator 25 to the light incident plane of the illuminating fiber 12 and allowing the reflection of return light emitted from the light incident plane of the illuminating fiber 12 to the light detecting section 62. In other words, the optical member 61 has the function of allowing the separation between the illuminating light emitted from the optical attenuator 25 to the light incident plane of the illuminating fiber 12 and the return light emitted from the light incident plane of the illuminating fiber 12.

The light detecting section 62 is made of a photodiode, for example. The light detecting section 62 has the function of generating an electrical signal that depends on the intensity of the return light received through the optical member 61 and outputting the generated signal to a controller 27.

The controller 27 of the present embodiment is configured to generate an image for one frame on the basis of R, G, and B signals outputted from a detection unit 23 within a time period between a time T1 and a time T2 and allow the generated image to be displayed on a monitor 4.

The controller 27 of the present embodiment is also configured to generate an image for one frame on the basis of R, G, and B signals outputted from the detection unit 23 within a time period from the time T2 to a time T3 and allow the generated image to be displayed on the monitor 4.

Furthermore, the controller 27 of the present embodiment is configured to sequentially detect a signal level of electrical signals outputted from the light detecting section 62 over the time period between the time T1 and the time T3 and then determine whether or not the detected fluctuations in the signal level correspond to a predetermined pattern.

Specifically, for example, once reading the information on a pattern of fluctuations in a signal level as shown in FIG. 21 from memory 26, the controller 27 determines whether or not the fluctuations in the signal level of the electrical signals outputted from the light detecting section 62 during the time period between the time T1 and the time T3 correspond to the pattern of fluctuations in the signal level included in the information read from the memory 26. FIG. 21 illustrates another example pattern of fluctuations in a signal level detected while illuminating light is properly emitted, the pattern being different from that illustrated in FIG. 9.

While the illuminating fiber 12 is swung in accordance with the trajectory of the spiral scanning pattern, the pattern of the fluctuations in the signal level illustrated in FIG. 21 is obtained depending on the intensity of return light generated when the light exit surface of the illuminating fiber 12 and the light exit surface of the lens 14*b* reflect illuminating light transmitted by the illuminating fiber 12.

Specifically, if the illuminating fiber 12 is being swung in accordance with the trajectory of the spiral scanning pattern, the pattern of the fluctuations in the signal level illustrated in FIG. 21 shows a maximum signal level SL3 at the time T1 where the intensity of the return light incident on the light detecting section 62 becomes largest; then, the signal level nonlinearly decreases during a time period between the times T1 and T2 where the intensity of the return light incident on the light detecting section 62 gradually decreases, and reaches a minimum signal level SL4 at the time T2 where the intensity of the return light incident on the light detecting section 62 becomes smallest. The signal level then nonlinearly increases during a time period between the times T2 and T3 where the intensity of the return light incident on the light detecting section 62 gradually increases, and reaches the maximum signal level SL3 again at the time T3 where the intensity of the return light incident on the light detecting section 62 becomes largest again.

If the controller 27 determines that the fluctuations in the signal level of the electrical signal outputted from the light detecting section 62 within the time period between the time T1 and the time T3 correspond to the pattern of the fluctuations included in the information read from the memory 26, then the controller 27 assumes that the illuminating light is properly emitted from the illuminating fiber 12 and continues the control for supplying the illuminating fiber 12 with illuminating light and the monitoring of the signal level of electrical signals outputted from the light detecting section 62.

By contrast, if the controller 27 determines that the fluctuations in the signal level of the electrical signal outputted from the light detecting section 62 within the time period between the time T1 and the time T3 do not correspond to the pattern of the fluctuations included in the information read from the memory 26, then the controller 27 assumes that an anomaly has occurred in the illuminating light emitted from the illuminating fiber 12 and carries out the control for lowering the quantity of illuminating light for the illuminating fiber 12.

Thus, according to the present embodiment, the quantity of illuminating light for the illuminating fiber 12 can be quickly lowered to a quantity of light that ensures the safety of a body in the event of an anomaly occurring in the illuminating light emitted from the illuminating fiber 12. This can reduce the risk of an adverse effect on the body caused by the illuminating light used for scanning an object.

It should be appreciated that the present invention is not limited to each of the above-described embodiments and may be modified as appropriate without deviating from the gist of the present invention.

What is claimed is:

1. An endoscope system comprising:
a light transmitting section configured to transmit illuminating light generated by a light source and emit the light from a light exit surface;
a light receiving section configured to receive return light of the light emitted from the light exit surface;
a light guiding section configured to allow the light emitted from the light exit surface to be incident on the light receiving section by totally reflecting return light from a subject or the emitted light at least one or more times;
a driving section configured to allow an end portion having the light exit surface of the light transmitting section to be swung to the subject during a first time period and to the light guiding section during a second time period so as to draw trajectories corresponding to predetermined scanning patterns;
a light detecting section configured to detect, of the light emitted from the light exit surface of the light transmitting section, the return light from the subject during the first time period, as a signal for image generation, and the light received through the light guiding section during the second time period, as a signal for emission quality determination;
a determination section configured to determine whether or not the pattern of fluctuations in a signal level detected by the light detecting section corresponds to a predetermined pattern of fluctuations; and
a control section configured to, if a determination result is that the pattern of fluctuations in the signal level within the second time period does not correspond to the predetermined pattern of fluctuations, perform control for lowering a quantity of the illuminating light supplied by the light source to the light transmitting section, to zero or a predetermined value.

2. The endoscope system according to claim 1, further comprising
an objective optical system configured to condense the light emitted from the light exit surface,
wherein the light guiding section is provided so as to cover at least a portion of a light incident plane of the light receiving section.

3. The endoscope system according to claim 2, wherein
the light receiving section is annularly provided, and
the light guiding section is formed of a transparent member having an annular ring shape or a fan shape.

4. The endoscope system according to claim 1, wherein
the light receiving section includes monitoring fibers for receiving light emitted from the light transmitting section during the second time period and light receiving fibers for receiving light emitted from the light transmitting section during the first time period.

5. The endoscope system according to claim 4, wherein
the light receiving section further includes a reflection member positioned so as to allow illuminating light emitted from the light transmitting section within the second time period to be reflected into the monitoring fibers.

6. The endoscope system according to claim 1, wherein
the predetermined scanning pattern is a spiral scanning pattern and the second time period is a time period for the end portion of the light transmitting section to be swung to an outermost circumference of the spiral scanning pattern.

7. The endoscope system according to claim 1, wherein
the predetermined scanning pattern is a raster scanning pattern and the second time period is a time period for the end portion of the light transmitting section to be swung to outermost segments of the raster scanning pattern.

8. The endoscope system according to claim 1, wherein
the predetermined scanning pattern is a Lissajous scanning
pattern and the second time period is a time period for
the end portion of the light transmitting section to be
swung to outermost segments of the Lissajous scanning
pattern.

\* \* \* \* \*